United States Patent
Safarevich

[11] Patent Number: 6,061,595
[45] Date of Patent: May 9, 2000

[54] LASER SPOT WELD WINDING TO CONNECTOR JOINT

[75] Inventor: Sergey Safarevich, Valencia, Calif.

[73] Assignee: Pacesetter, Inc., Sylmar, Calif.

[21] Appl. No.: 09/225,135

[22] Filed: Jan. 4, 1999

[51] Int. Cl.$^7$ .................................................. A61N 1/05
[52] U.S. Cl. .......................... 607/37; 439/909; 439/874
[58] Field of Search .............................. 607/37; 439/909, 439/874

[56] References Cited

U.S. PATENT DOCUMENTS

| | | | |
|---|---|---|---|
| 1,390,596 | 9/1921 | Thornton, Jr. . | |
| 1,745,180 | 1/1930 | Mischler | 439/874 |
| 1,908,859 | 5/1933 | O'Neill | 439/874 |
| 1,977,846 | 10/1934 | Febrey | 29/148 |
| 2,878,461 | 3/1959 | Friedmann et al. | 339/275 |
| 3,656,092 | 4/1972 | Swengel, Sr. et al. | 339/213 T |
| 3,676,575 | 7/1972 | Weaver et al. | 174/94 R |
| 4,161,952 | 7/1979 | Kinney et al. | 128/786 |
| 4,352,714 | 10/1982 | Patterson et al. | 156/626 |
| 4,360,031 | 11/1982 | White | 128/786 |
| 4,784,161 | 11/1988 | Skalsky et al. | 128/785 |
| 4,844,099 | 7/1989 | Skalsky et al. | 128/785 |
| 4,917,106 | 4/1990 | Olivier | 128/785 |
| 4,966,565 | 10/1990 | Dohi | 439/874 |
| 5,115,818 | 5/1992 | Holleman et al. | 128/784 |
| 5,259,395 | 11/1993 | Li | 607/131 |
| 5,385,578 | 1/1995 | Bush et al. | 607/122 |
| 5,489,294 | 2/1996 | McVenes et al. | 607/120 |
| 5,522,872 | 6/1996 | Hoff | 607/119 |
| 5,522,874 | 6/1996 | Gates et al. | 607/127 |
| 5,522,875 | 6/1996 | Gates et al. | 607/127 |
| 5,569,883 | 10/1996 | Walter et al. | 174/84 R |
| 5,571,146 | 11/1996 | Jones et al. | 607/37 |
| 5,649,974 | 7/1997 | Nelson et al. | 607/122 |
| 5,676,694 | 10/1997 | Boser et al. | 607/122 |
| 5,716,390 | 2/1998 | Li | 607/127 |
| 5,728,149 | 3/1998 | Laske et al. | 607/122 |
| 5,746,616 | 5/1998 | Mar | 439/245 |
| 5,869,804 | 2/1999 | Mueller et al. | 607/37 |

*Primary Examiner*—Kennedy Schaetzle

[57] ABSTRACT

A technique is presented for joining an elongated wound element having a plurality of filars and a mating component of a body implantable lead assembly. The wound element has a longitudinally extending interior passage and an end portion extending to a terminal end. The mating component includes a shoulder and an integral post extending away therefrom having an outer surface for receiving the end portion of the wound element, the diameter of the outer surface being smaller than that of the shoulder and larger than the diameter of the interior passage of the wound element. At a location spaced from the terminal end of the wound element, the end portion of the wound element and the receiving portion of the mating component are thermally fused together. This is performed by targeting a laser beam on the end portion of the wound element at a location spaced from the terminal end thereof to melt the wound element and the receiving portion of the mating component and thereby create a weld nugget. In actual fact, the laser beam is targeted at a plurality of circumferentially spaced locations about the end portion of the wound element, the number of such locations being determined by the following relationship:

$$N = 1 + 2.5 \times d \times F / D_w$$

where
  d = wire diameter,
  $D_w$ = weld spot diameter,
  F = number of filars
when F > 2 and $D_w/d \geq 2$.

The wound element and the mating component may be fabricated of the same or dissimilar alloys.

14 Claims, 2 Drawing Sheets

LASER SPOT WELD WINDING TO CONNECTOR JOINT

FIELD OF THE INVENTION

The present invention relates generally to lead assemblies for connecting implantable medical devices with selected body tissue to be stimulated by such devices, and more particularly to techniques for providing a secure electrical and mechanical connection between wound elements, such as coil conductors, and mating parts such as electrodes, sensors and the like, employed within such lead assemblies.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. The appended claims are not intended to be limited, however, to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing or for sensing electrical signals produced by the heart or for both pacing and sensing in which case a single lead serves as a bi-directional pulse transmission link between the pacemaker and the heart. An endocardial type lead, that is, a lead which is inserted into a vein and guided therethrough into a cavity of the heart, includes at its distal end an electrode designed to contact the endocardium, the tissue lining the inside of the heart. The lead further includes a proximal end having a connector pin adapted to be received by a mating socket in the pacemaker. A flexible, coiled or wound conductor surrounded by an insulating tube or sheath couples the connector pin at the proximal end with the electrode at the distal end.

A primary concern with laser welding of two metals is that there must exist a balance between energy to be delivered to the metal masses. Current connections between the electrode mount/connector to the winding (usually multifilar) employ a circumferential weld. The problem with laser welding of this type is that it is necessary to heat a large mass (the connector) in order to obtain an optimum melt. This technique is time-consuming, has a tendency of overheating of components, and has inconsistent results leading to questionable reliability.

Alternately, spot welding has the advantages of less concern for overheating and is less time-consuming. However, current spot welding techniques have had inconsistent results. Filars do not always line up appropriately and/or don't get welded consistently because specific energy balance is required and is difficult to achieve.

To compensate, spot welds can be performed on each end of the wires. Disadvantages of this technique include misbalancing of energy as well as the time consumed in targeting the beam to the exact positions needed.

Each of these techniques have been implemented with such inconsistent results that throughput in production has varied from 95% to 0%.

What is needed, therefore, is a high reliability weld connection with increased manufacturability (i.e., repeatability and reduced time of assembly).

The present invention is directed towards a method of determining the appropriate number of spot welds based on the number of filars, the number of turns, the spot weld diameter, and the desirable location of the spot weld.

Another problem associated with connections between wound elements and mating components in present day lead assemblies arises from the use of different alloys for the wound elements and mating components. Since dissimilar alloys have different thermal properties, including melt temperatures, such connections are difficult to weld. Moreover, as lead sizes decrease, problems of manufacturability arise. This is particularly true where crimping is employed to secure the wound component to a mating element. See, for example, U.S. Pat. No. 4,953,564 which discloses a cardiac pacing lead having an extendible fixation helix electrode that is mechanically and electrically connected to a rotatable conductor coil by squeezing the helix and coil together between a crimping sleeve and a crimping core. As the sizes of body implantable leads and their constituent parts become smaller, crimping becomes more difficult because the crimping tools cannot be made sufficiently small. Moreover, the same number of lead windings are not always subjected to the crimping action so that failure stress differs from lead to lead.

Some selective examples of the patented prior art bear a brief mention are U.S. Pat. No. 5,569,883 to Walter et al., which discloses laser welding a wire coil to an intermediate ring or the like; U.S. Pat. No. 5,571,146 to Jones et al., which discloses laser welding dissimilar materials by means of an aperture within a lead; and U.S. Pat. No. 5,385,578 to Bush et al., which discloses laser welding a wire coil to a sleeve.

It was with knowledge of the foregoing state of the technology that the present invention has been conceived and is now reduced to practice.

SUMMARY OF THE INVENTION

A technique is presented, according to the invention, for joining an elongated wound element having a plurality of filars and a mating component of a body implantable lead assembly. The wound element has a longitudinally extending interior passage and an end portion extending to a terminal end. The mating component includes a shoulder and an integral post extending away therefrom having an outer surface for receiving the end portion of the wound element, the diameter of the outer surface being smaller than that of the shoulder and larger than the diameter of the interior passage of the wound element. At a location spaced from the terminal end of the wound element, the end portion of the wound element and the receiving portion of the mating component are thermally fused together. This is performed by targeting a laser beam on the end portion of the wound element at a location spaced from the terminal end thereof to melt the wound element and the receiving portion of the mating component and thereby create a weld nugget. In actual fact, the laser beam is targeted at a plurality of circumferentially spaced locations about the wound element, the number of such locations being determined by the following relationship:

$$N = 1 + 2.5 \times d \times F / D_w$$

where
 d = wire diameter
 $D_w$ = weld spot diameter
 F = number of filars
when F > 2 and $D_w / d \geq 2$.

The wound element and the mating component may be fabricated of the same or dissimilar alloys.

As already noted, a primary purpose of the invention is to improve a laser weld between a winding and a connector and to achieve this result, the laser beam energy should be distributed equally between the wire and the connector. The common, or known, weld joint typically comprises a winding screwed onto a cylindrical connector. The very last wind (that is, the terminal end of the wire) is set against a shoulder. The shoulder and the last wind are then welded together in an appropriate manner (see FIG. 1).

However, the problem addressed by the present invention resides in the fact that the connector requires more laser energy to melt than does the wire. During welding, a laser beam melts both the connector and the wire (winding). The wire has less metal mass than does the connector. As such, the wire accumulates heat very quickly and the wire can melt easily. The wire melted metal spreads over the connector forming the weld spot. A lack of melted metal creates wire "neck down" and negative weld reinforcement, which reduces the strength of the resulting weld joint. The connector has much more metal mass, which means it draws the heat out of the weld region. This makes it difficult to melt the metal to fuse components together. Therefore, the connector requires more laser energy to melt than does the wire. To achieve a reliable weld, the beam energy must be specifically balanced between the connector and the wire. The proper beam targeting requires placement of the laser beam not equally on the joint such that more energy is on the shoulder side than on the wire. It is difficult for the line operator to target the laser beam on the joint properly.

A difference in material thermal properties magnifies the energy balance problem. For example, platinum requires much more energy to melt than MP35N. If a joint consists of MP35N wire and a platinum connector it will need a greater misbalance of energy to melt the components equally. Proper beam targeting required to achieve a solid weld becomes more critical with dissimilar materials than with similar materials.

A primary feature, then, of the present invention is the provision of a significantly improved technique for providing a secure electrical and mechanical connection between wound elements, such as coil conductors, and mating parts such as electrodes, sensors and the like, employed within such lead assemblies.

Another feature of the present invention is the provision of such a technique employing a laser.

Still another feature of the present invention is the provision of such a technique which can achieve a satisfactory connection whether or not the alloys of which the components are fabricated are the same or dissimilar.

Yet another feature of the present invention is the provision of a technique of joining a longitudinally extending wound element and a mating component of a body implantable lead assembly, the wound element having a longitudinally extending interior passage and an end portion adapted to be received by a portion of the mating component, the receiving portion of the mating component being configured to receive the end portion of the wound element.

Still another feature of the present invention is the provision of such a technique which includes placing an end portion of the wound element about the receiving portion of the mating component, then thermally fusing the end portion of the wound element and the receiving portion of the mating component at a location spaced from the terminal end of the wound element.

Yet another feature of the present invention is the provision of such a technique which includes targeting a laser beam on the end portion of the wound element at a location spaced from the terminal end thereof to melt the wound element and the receiving portion of the mating component and thereby create a weld nugget.

Yet another feature of the present invention is the provision of such a technique which the mating component includes a shoulder and a post integral therewith and extending away therefrom having an outer surface for receiving the end portion of the wound element, the diameter of the outer surface being smaller than that of the shoulder, the end portion of the wound element being advanced until the terminal end thereof engages the shoulder.

Still a further feature of the present invention is the provision of such a technique according to which the laser beam is targeted at a plurality of circumferentially spaced locations about the wound element, the number of such locations being determined by the following relationship:

$$N = 1 + 2.5 \times d \times F / D_w$$

where $d$=wire diameter, $D_w$=weld spot diameter, and $F$=number of filars when $F > 2$ and $D_w/d \geq 2$.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Of primary concern with laser welding of two metals is that there must exist a balance between energy to be delivered to the metal masses. Known connections between lead wire ends (usually a multifilar winding) to the shoulder of an electrode mount or connector is a circumferential weld. The problem with this type of weld is that the laser beam must heat a large mass of connector in order to obtain a satisfactory melt to heat and cause fixation of the wire ends. This technique is time consuming, has a tendency of overheating of the components being joined, particularly the wire winding, and has inconsistent results (i.e., reliability defects).

Alternately, spot welding has the advantages of less concern for overheating. However, current techniques of spot welding (for example, a weld on each wire end) have had inconsistent results. Filars do not always line up appropriately and/or don't get welded consistently because specific energy balance is required and is difficult to achieve. Disadvantages of this technique include misbalancing of energy; also, it is time consuming to target the energy beam at the exact locations needed.

Each of these techniques has been implemented with such inconsistent results, that throughput in production varies greatly. What is needed is a high reliability weld connection with increased manufacturability, that is, repeatability and reduced assembly time. These benefits are provided by the present invention.

Figure 1:
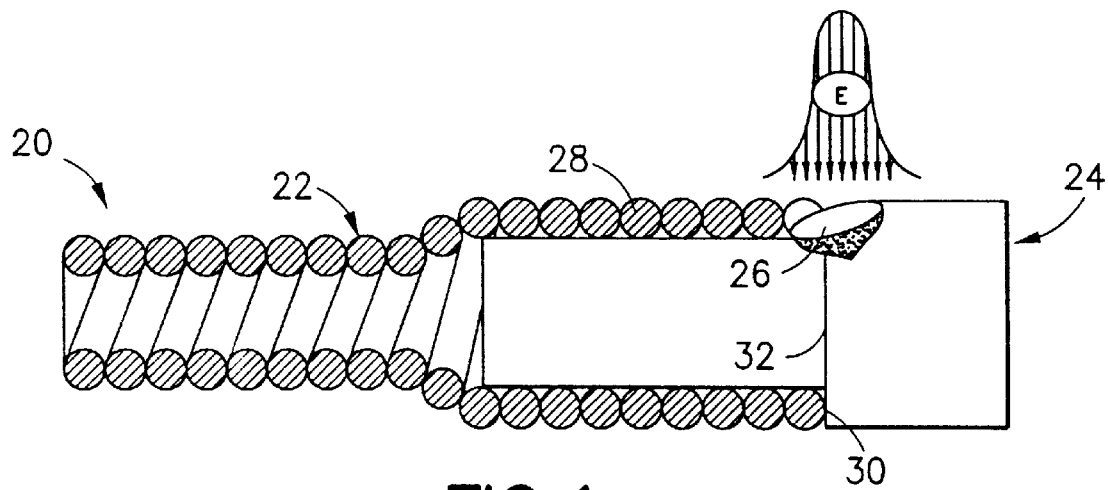
FIG. 1 is a diagrammatic side elevation view, partially cut away and in section, of a known laser weld assembly between a multi wire winding and a connector.

Turn now to the drawings and, initially, to FIG. 1 which generally illustrates a conventional circumferential laser weld assembly 20 between a multi wire winding 22 and a connector 24. To achieve this weld assembly 20, weld spots 26 obtained by use of a laser represented by a beam E, should be distributed around the periphery of the connector to melt together each wire strand 28 and the connector 24 itself. The common weld assembly comprises the winding 22 screwed or otherwise applied onto the cylindrical connector 24. The very last wind (wire ends 30) butts up against a shoulder 32 of the connector. The shoulder 32 and the last wind (wire ends 30) are thereby welded together.

As earlier explained, the connector 24 requires more laser energy to melt than does the wire strand 28 and the weld region needs more melted metal to increase strength of the weld assembly. During welding, the laser beam E melts both the connector 24 and the winding 22. The wire possesses less metal mass than does the connector. As such, the winding accumulates heat very quickly and the wire strands 28 can melt easily. The melted metal from the winding spreads over the connector forming the weld spot 26. A lack of melted metal creates wire "neck down" and negative weld reinforcement, which reduces the strength of weld joint. The connector has much more metal mass, which means it draws the heat out of the weld area. Unfortunately, this condition makes it difficult to melt the metal to fuse the components together. Therefore, the connector requires more energy from the laser beam E to melt than does the winding. To achieve a reliable weld, the beam energy must be specifically balanced between the connector and the winding. The proper beam targeting requires placement of the laser beam unequally on the joint such that more energy is on the shoulder side than on the wire. However, it is difficult for the assembly line operator to properly target the laser beam on the joint. A difference in material thermal properties further magnifies the energy balance problem. For example, platinum requires much more energy to melt than does MP35N, a high corrosion resistant stainless steel used for implantable devices including leads. If a joint comprises MP35N wire and a platinum connector it will need a greater misbalance of energy to melt the components equally. Proper beam targeting required to achieve a solid weld becomes more critical with dissimilar materials than with similar materials.

Figure 2:
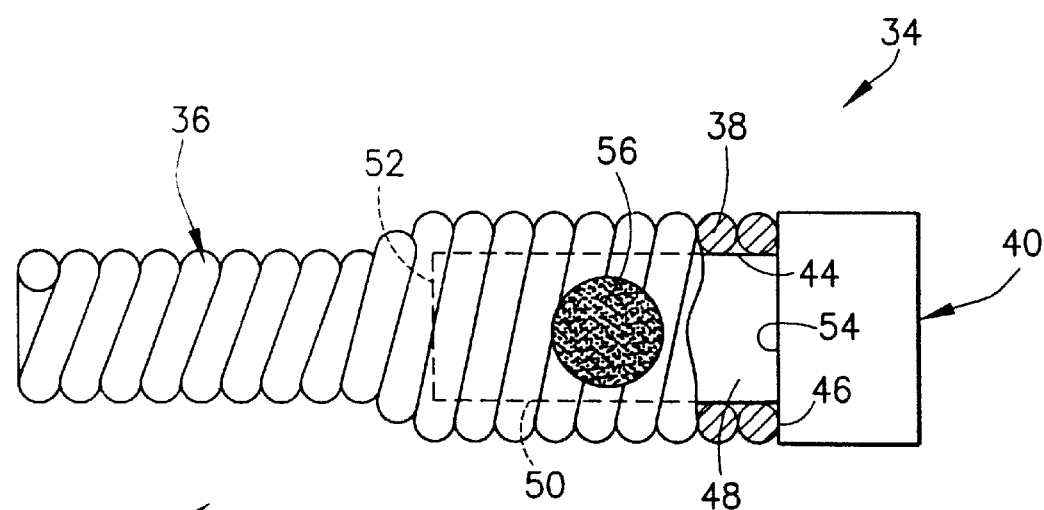
FIG. 2 is a diagrammatic plan view, similar to FIG. 1 but illustrating a laser weld assembly embodying the invention.
Figure 3:
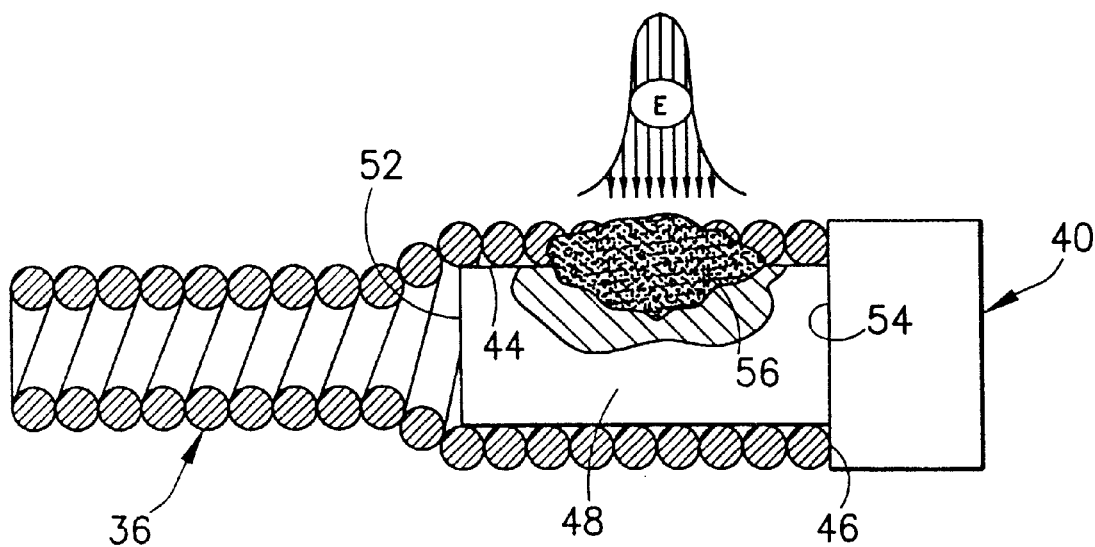
FIG. 3 is a diagrammatic side elevation view of the laser weld assembly embodying the invention and illustrated in FIG. 2.

For a description of the invention, turn now to FIGS. 2 and 3. In this instance, a weld assembly or joint 34 serves to connect a longitudinally extending wound element 36 formed of coiled wire strands 38 and a mating connector, or component 40, of a body implantable lead assembly 42. The wound element 36 has an interior passage 44 and a terminal end 46. The mating component 40 includes a post 48 for receiving the terminal end 46 of the wound element 36. The post 48 has an outer surface 50 and a terminal end 52. The terminal end 46 of the wound element 36 is disposed about the post 48 and advanced over the terminal end 52 until it abuts a shoulder 54 on the mating component 40. At a location spaced inboard from the terminal end 46, the end portion of the wound element 36 is thermally fused to the receiving portion, or post 48, of the mating component 40.

Preferably, the thermal fusing operation is performed by targeting a laser beam E, see FIG. 3, on the end portion of the wound element at a location spaced from the terminal end 46 to melt the wound element 36 and the post 48 in that vicinity and thereby create a weld nugget 56. The high density laser beam penetrates through the wound element 36 to the post 48 of the mating component 40. During the pulse, the laser beam melts the wires and then post, vaporizing some portion of the metal. The vapor pressure pushes the melted metal on the peripheral part of the weld spot, fusing the wires together.

Since the joint configuration (wound element 36 above the mating component 40) does not require a specific energy balance, the weld joint can be created easily.

The strength of the resulting joint, with each wire welded to the connector, can be achieved by equally distributing a certain number of weld spots around the winding and connector. Furthermore, while the wound element 36 and its mating component 40 may be made from the same material, the invention enables welded joints to be made easily and rapidly even if they are of dissimilar materials.

Figure 4:
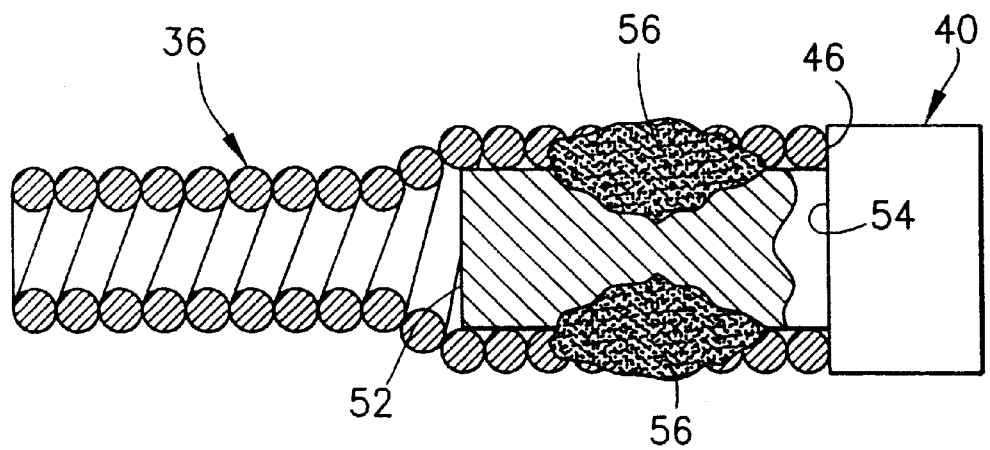
FIG. 4 is a diagrammatic side elevation view, similar to FIG. 3 but illustrating a pair of welds.

While a single weld nugget may suffice, it is desirable to targeting the laser beam at a plurality of circumferentially spaced locations (see FIG. 4) about the wound element, especially when the wound element has multiple filars. The number of such locations being determined by the following relationship:

$$N=1+2.5 \times d \times F/D_w$$

where
d=wire diameter,
$D_w$=weld spot diameter, and
F=the number of filars
when F>2 and $D_w/d \geq 2$.

In this regard, consider several examples:

EXAMPLE 1

Assume, that the wire diameter is d=0.004", number of filars is F=4 and the weld spot diameter is D=0.020". Then the minimum number of nuggets required is N=1+2, thus N=3.

EXAMPLE 2

Assume, that the wire diameter is d=0.004", the number of filars is F=3 and the weld spot diameter is D=0.018". Then the minimum number of nuggets required is N=1+1.6, thus N=3, after rounding.

EXAMPLE 3

Assume, that the wire diameter is d=0.008", the number of filars is F=2 and the weld nugget diameter is D=0.030". Then, the minimum number of nuggets required is N=1+1.3, thus N=2, after rounding.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A method of joining an elongated wound element and a mating component of a body implantable lead assembly, the wound element having a longitudinally extending interior passage and an end portion extending to a terminal end adapted to be received by a portion of the mating component, the receiving portion of the mating component being configured to receive the end portion of the wound element, the method comprising the steps of:

(a) placing the end portion of the wound element about the receiving portion of the mating component; and (b) at a location spaced from the terminal end of the wound element, thermally fusing the end portion of the wound element and the receiving portion of the mating component by directly applying energy to the wound element.

2. The method, as set forth in claim 1, wherein the wound element and the mating component are fabricated of the same alloy.

3. The method, as set forth in claim 1, wherein the wound element and the mating component are fabricated of dissimilar alloys.

4. The method, as set forth in claim 1, wherein the receiving portion of the mating component has a diameter which is larger than the diameter of the interior passage of the wound element.

5. The method, as set forth in claim 1, wherein step (b) includes the step of:

(c) targeting a laser beam on the end portion of the wound element at a location spaced from the terminal end thereof to melt the wound element and the receiving portion of the mating component and thereby create a weld nugget.

6. The method, as set forth in claim 5:

wherein the receiving portion of the mating component includes a post having an outer surface for receiving the end portion of the wound element;

wherein the wound element includes a coil having a plurality of filars; and wherein step (c) includes the step of:

(d) targeting the laser beam at a plurality of circumferentially spaced locations about the end portion of the wound element.

7. A method of joining an elongated wound element and a mating component of a body implantable lead assembly, the wound element having a longitudinally extending interior passage and an end portion extending to a terminal end adapted to he received by a portion of the mating component, the receiving portion of the mating component being configured to receive the end portion of the wound element, the method comprising the steps of:

(a) placing the end portion of the wound element about the receiving portion of the mating component;

(b) at a location spaced from the terminal end of the wound element, thermally fusing the end portion of the wound element and the receiving portion of the mating component;

(c) targeting a laser beam at a plurality of circumferentially spaced locations about the end portion of the wound element at a location spaced from the terminal end thereof to melt the wound element and the receiving portion of the mating component and thereby create a weld nugget;

wherein the receiving portion of the mating component includes a post having an outer surface for receiving the end portion of the wound element and the wound element includes a coil having a plurality of filars; and wherein step (c) includes the step of (d) targeting the laser beam at a plurality of circumferentially spaced locations about the end portion of the wound element, the number of such locations being determined by the following relationship:

$$N=1+2.5 \times d \times F/D_w$$

where
    d=wire diameter
    $D_w$=weld spot diameter
    F=number of filars
when F>2 and $D_w/d=2$.

8. A method of joining an elongated wound element and a mating component of a body implantable lead assembly, the wound element having a longitudinally extending interior passage and an end portion extending to a terminal end adapted to he received by a portion of the mating component, the receiving portion of the mating component being configured to receive the end portion of the wound element, the method comprising the steps of:

(a) placing the end portion of the wound element about the receiving portion of the mating component;

(b) at a location spaced from the terminal end of the wound element, thermally fusing the end portion of the wound element and the receiving portion of the mating component;

wherein the mating component includes a shoulder and a post integral therewith and extending away therefrom having an outer surface for receiving the end portion of the wound element, the diameter of the outer surface being smaller than that of the shoulder; and wherein step (a) includes the step of:

(c) advancing the end portion of the wound element until the terminal end thereof engages the shoulder.

9. A joint connecting an elongated wound element and a mating component of a body implantable lead assembly, the wound element having an interior passage and an end portion extending to a terminal end, the mating component having a post for receiving the end portion of the wound element, the post having an outer surface, the end portion of the wound element being disposed about the post and being in engagement with the outer surface thereof, the post and the end portion of the wound element being integrally joined together by mutual melting of the wound element and the post caused by targeting a laser beam directly on the end portion of the wound element at a location spaced from the terminal end thereof thereby creating a weld nugget.

10. The joint, as set forth in claim 9, wherein the wound element and the post are made of the same metallic alloy.

11. The joint, as set forth in claim 9, wherein the wound element and the post are made of dissimilar alloys.

12. The joint, as set forth in claim 9, wherein the outer surface of the post has a generally cylindrical configuration with a diameter which is larger than the diameter of the interior passage of the wound element.

13. A joint connecting an elongated wound element and a mating component of a body implantable lead assembly, the wound element having an interior passage and an end portion extending to a terminal end, the mating component having a post for receiving the end portion of the wound element, the post having an outer surface, the end portion of the wound element being disposed about the post and being in engagement with the outer surface thereof, the post and the end portion of the wound element being integrally joined together by mutual melting of the wound element and the post caused by targeting a laser beam on the end portion of the wound element at a location spaced from the terminal end thereof thereby creating a weld nugget;

wherein the mating component includes a shoulder and a post integral therewith and extending away therefrom having an outer surface for receiving the end portion of the wound element, the diameter of the outer surface being smaller than that of the shoulder; and wherein the end portion of the wound element is advanced onto the mating component until the terminal end thereof engages the shoulder.

14. A joint connecting an elongated wound element and a mating component of a body implantable lead assembly, the wound element having an interior passage and an end portion extending to a terminal end, the mating component having a post for receiving the end portion of the wound element, the post having an outer surface, the end portion of the wound element being disposed about the post and being in engagement with the outer surface thereof, the post and the end portion of the wound element being integrally joined together by mutual melting of the wound element and the post caused by targeting a laser beam on the end portion of the wound element at a location spaced from the terminal end thereof thereby creating a weld nugget;

wherein the wound element includes a coil having a plurality of filars; and wherein the laser beam is targeted at a plurality of circumferentially spaced locations about the end portion of the wound element, the number of such locations being determined by the following relationship:

$$N = 1 + 2.5 \times d \times F / D_w$$

where $d$ = wire diameter $D_w$ = weld spot diameter

F = number of filars when F>2 and $D_w/d=2$.

* * * * *